(12) United States Patent
Jansen et al.

(10) Patent No.: US 11,382,317 B2
(45) Date of Patent: Jul. 12, 2022

(54) CLIMATE CONTROL SYSTEM FOR INSECT FARMING

(71) Applicant: Protix B.V., Dongen (NL)

(72) Inventors: Jaco Jansen, Breda (NL); Raymond Joseph Leushuis, Alphen (NL); Jaap van Kilsdonk, Veldhoven (NL); Eric Holland Schmitt, Antwerp (BE); Johannes Dijkshoorn, 's-Hertogenbosch (NL)

(73) Assignee: Protix B.V., Dongen (NL)

( * ) Notice: Subject to any disclaimer, the term of this patent is extended or adjusted under 35 U.S.C. 154(b) by 21 days.

(21) Appl. No.: 16/954,540

(22) PCT Filed: Dec. 21, 2018

(86) PCT No.: PCT/NL2018/050868
§ 371 (c)(1),
(2) Date: Jun. 17, 2020

(87) PCT Pub. No.: WO2019/125163
PCT Pub. Date: Jun. 27, 2019

(65) Prior Publication Data
US 2020/0337281 A1    Oct. 29, 2020

(30) Foreign Application Priority Data
Dec. 22, 2017  (NL) ...................... 2020175

(51) Int. Cl.
*A01K 67/033*  (2006.01)
*A01K 1/00*    (2006.01)

(52) U.S. Cl.
CPC .......... *A01K 67/033* (2013.01); *A01K 1/0058* (2013.01)

(58) Field of Classification Search
CPC .................... A01K 67/0033; A01K 1/0058
See application file for complete search history.

(56) References Cited

U.S. PATENT DOCUMENTS 5,036,797 A * 8/1991 Koozer ................ A01K 1/0058
                                                           119/448
8,602,837 B1 * 12/2013 Allan ................... A01K 67/033
                                                             449/1
(Continued)

FOREIGN PATENT DOCUMENTS

CA    2979709 A1 *  9/2016 .......... A01K 67/033
CA    3023366 A1 *  9/2018 .......... A01K 1/0076
(Continued)

*Primary Examiner* — Monica L Barlow
*Assistant Examiner* — Aaron M Rodziwicz
(74) *Attorney, Agent, or Firm* — N.V. Nederlandsch Octrooibureau; Catherine A. Shultz

(57) ABSTRACT

The invention relates to a climate control device for controlling the temperature and humidity of air supplied to colonies of insects cultured in an industrial scale insect farm. In particular, the invention relates to a controllable air conditioning system involving a network of pipes connecting at least one cluster having at least one insect farming cage, such that air is conditionable in the cages at the cluster level. More specifically, the invention relates to a system having a central main air conditioning facility providing temperature conditioned air and absolute air humidity conditioned air to each of a number of local air conditioning devices, each separate local air conditioning device providing temperature conditioned air and absolute air humidity conditioned air to each of a plethora of clusters of insect breeding cages separately, said cages housed in a temperature conditioned farming room. This way, insects in cages housed in farming rooms are farmed under improved conditions with regard to minimized cage-to-cage temperature differences and differences in relative air humidity, due to the use of the climate control device of the invention.

20 Claims, 5 Drawing Sheets

(56) References Cited

U.S. PATENT DOCUMENTS

| | | | |
|---|---|---|---|
| 2011/0146582 A1* | 6/2011 | Lemmon | A01K 1/0052 |
| | | | 119/448 |
| 2017/0325431 A1* | 11/2017 | Leo | A23K 50/90 |
| 2018/0007875 A1* | 1/2018 | Hall | A01K 7/02 |
| 2018/0049414 A1* | 2/2018 | Leo | A23K 20/163 |
| 2018/0369867 A1* | 12/2018 | Sobecki | B07B 1/06 |
| 2020/0275643 A1* | 9/2020 | Metlitz | A01K 1/0076 |

FOREIGN PATENT DOCUMENTS

| | | | |
|---|---|---|---|
| FR | 3034623 A1 * | 10/2016 | A01K 67/033 |
| JP | 06257789 A | 9/1994 | |
| RU | 2033047 C1 | 4/1995 | |
| WO | 2014/171829 A1 | 10/2014 | |
| WO | WO-2014171829 A1 * | 10/2014 | A01K 29/005 |
| WO | 2015023178 A1 | 2/2015 | |
| WO | WO-2016153340 A2 * | 9/2016 | A01K 67/033 |
| WO | WO-2019059760 A1 * | 3/2019 | A01K 1/03 |

* cited by examiner

CLIMATE CONTROL SYSTEM FOR INSECT FARMING

TECHNOLOGICAL FIELD

The invention relates to a climate control device for controlling the temperature and humidity of air supplied to colonies of insects cultured in an industrial scale insect farm. In particular, the invention relates to a controllable air conditioning system comprising a network of pipes connecting at least one cluster comprising at least one insect farming cage, such that air is controllably conditioned in the cages at the cluster level. More specifically, the invention relates to a system comprising a central main air conditioning facility providing temperature conditioned air and absolute air humidity conditioned air to each of a number of local air conditioning devices, each separate local air conditioning device providing temperature conditioned air and absolute air humidity conditioned air to each of a plethora of clusters of insect breeding cages separately, said cages housed in an temperature conditioned farming room. This way, insects in cages housed in farming rooms are farmed under improved conditions with regard to minimized cage-to-cage temperature differences and differences in relative air humidity, due to the use of the climate control device of the invention.

BACKGROUND

Insects are considered one of the most promising means for protein and for organic residual recovery. Prominent examples of species proposed for the indicated applications include the black soldier fly (*Hermetia illucens*), the house fly (*Musca domestica*), and the mealworm (*Tenebrio molitor* L.).

Methods improving the efficiency of insect farming relating to improvements in controllability of farming conditions and therewith as a direct consequence farming efficiency and yield, are highly desired.

Up till now, economics of scale with regard to insect farming is only applicable in theory, since for many, if not all, of the steps and activities involved in insect farming that would be economically feasible, suitable machinery, equipment, farming facilities, etc., with regard to controllable farming conditions and predictable farming results, and with regard to optimal use of available insect farming capacity, are not available to the required extent.

Currently, low-tech insect farming occurs in farming rooms which are sub-optimally climate controlled at best, such that micro-climates are present within a single farming room, the differences between such micro-climates giving rise to cumbersome differences and delays in farming results and unreliable and unpredictable outcomes of farming activities. It is well known in the art that controlling the climate in an insect farming room with regard to uniform temperature and uniform relative humidity of the air in the environment in which insects are bred, is a cumbersome task to the farmer since currently available tools and devices provide far from optimal results when steady air conditioning is assessed. Since a temperature difference of for example 2-3° C. in an insect farming room is commonly at hand, this temperature difference for example measured between air surrounding insect cages in the back of a room and air surrounding insect cages in the front of a room, for example located in closer proximity of a temperature control device of an air conditioning device in the farming room, large differences in development of the insects occurs. Temperature differences at various locations within an insect farming room are commonly even more apparent when the temperature at floor level and above is compared to the temperature near the ceiling and below, since warm air rises, easily creating a vertical temperature gradient in a room.

This drawback of the occurrence of micro-climates in farming rooms results in largely uncontrollable farming outcomes and for example in large differences in the speed and stage of insect colony development when compared cage-to-cage within a single farming room and/or when colonies farmed in parallel or consecutively are farmed in separate farming rooms and/or when colonies are farmed consecutively within the same farming room. The drawback of the occurrence of temperature gradients in an insect farming room comprising the cages with colonies of insects becomes even more apparent when scaling up insect farming in relatively large farming rooms. That is to say, an intra-room climate heterogeneity tends to increase as the size and volume of the farming room increase, which size increase occurs as farming scale increases in order to achieve industrial production.

For example, international patent application WO 2015/023178 describes a cage for breeding insects, wherein the cage is provided with at least one wall which is gas-permeable for allowing fresh air to enter the cage. WO 2015/023178 furthermore describes that the moisture and temperature above the cage is controlled with the use of a control system, although no details are provided as to for example the tolerance with regard to the controlled temperature and moisture outside the cage, or inside the cage.

Thus, methods and means for efficacious and beneficial insect farming at industrial-scale, are at present not available in the art.

SUMMARY OF THE INVENTION

It is a first goal of the present invention to take away the above mentioned disadvantages, or at least to provide a useful alternative to the state of the art.

It is an object of the current invention to provide tools and equipment for farming of insects such as pupae and adult insects, which tools and equipment have the beneficial characteristics required for solving the problem of insect cage-to-cage temperature differences and/or insect cage-to-cage differences in water content of the air surrounding farmed insects.

It is an object of the current invention to provide a means for farming insects, preferably pupae and/or adult insects, which bears the opportunity to farm a plethora of colonies of said insects in parallel or in consecutive order, within the same farming room, or in separate farming rooms, such that the aimed results and the yield of the insect farming activities with regard to colonies originating from different cages and/or different farming cycles in time, is more predictable, is improved and/or increased and/or is suffering from less fall-out due to for example detrimental cage-to-cage temperature differences, and/or differences in relative air humidity, and/or even too dry air or air comprising too high moisture content.

In addition, it is an object of the current invention to provide a means for farming insects, preferably pupae and/or adult insects for retrieving the precious eggs form gravid female insects such as black soldier flies, which reduces the risk for cage to cage biological contamination, and/or cage to cage odor contamination, problems occurring when applying current small-scale farming equipment comprising cages in open air communication with the environment.

It is another or alternative object to provide a means for improved and efficient temperature control and/or air humidity control on a cage-to-cage basis when a plethora of cages is considered within a single insect farming room, and/or when batches of insect farming cages in separate insect farming rooms are considered, and to provide a means for conditioning the air in at least one selected cage while temporarily the air in at least one further cage is not conditioned, using a device for providing temperature- and/or moisture conditioned air to insect farming cages.

At least one of the above objectives is achieved by an insect farm climate control system comprising a central air conditioning unit coupled to at least one local climate control system comprising a cage climate control device for conditioning the air inside at least one insect cage, according to the invention.

The objective of improved temperature control and improved air humidity control inside each and every insect farming cage throughout an extended period of time and when considering insect farming in cages in parallel or in consecutive order, is achieved by application of an adult insect cage climate control system of the invention. That is to say, the inventors established that the temperature difference is improvingly and surprisingly small, i.e. as low as 2° C. or less, or even as low as 1° C. or less, when any two cages within a farming room are considered or any two cages in use for insect farming in two separate farming rooms, when either farmed in parallel or in consecutive order, when applying the insect farm climate control system of the invention. The same holds true for observed improvingly and surprisingly small differences in relative air humidity on a cage-to-cage basis throughout farming cycles, when the adult insect cage climate control system of the invention is applied for farming insects, e.g. pupae and/or adult insects, for the purpose of collecting insect eggs.

The present invention will be described with respect to particular embodiments and with reference to certain drawings in FIG. 1-5, but the invention is not limited thereto but only by the claims. The drawings described are only schematic and are non-limiting. In the drawings, the size of some of the elements may be exaggerated and not drawn on scale for illustrative purposes. The dimensions and the relative dimensions do not necessarily correspond to actual reductions to practice of the invention.

Furthermore, the terms first, second, third and the like in the description and in the claims, are used for distinguishing between similar elements and not necessarily for describing a sequential or chronological order. The terms are interchangeable under appropriate circumstances and the embodiments of the invention can operate in other sequences than described or illustrated herein.

Moreover, the terms top, bottom, side, front, back, over, under and the like in the description and the claims are used for descriptive purposes and not necessarily for describing relative positions. The terms so used are interchangeable under appropriate circumstances and the embodiments of the invention described herein can operate in other orientations than described or illustrated herein, unless specified otherwise.

The embodiments of the invention described herein can operate in combination and cooperation, unless specified otherwise.

Furthermore, the various embodiments, although referred to as "preferred" or "e.g." or "for example" or "in particular" are to be construed as exemplary manners in which the invention may be implemented rather than as limiting the scope of the invention.

The term "comprising", used in the claims, should not be interpreted as being restricted to the elements or steps listed thereafter; it does not exclude other elements or steps. It needs to be interpreted as specifying the presence of the stated features, integers, steps or components as referred to, but does not preclude the presence or addition of one or more other features, integers, steps or components, or groups thereof. Thus, the scope of for example the expression "a system comprising A and B" or for example "a device comprising C and D" should not be limited to systems and devices consisting only of components A and B or C and D, rather with respect to the present invention, the only enumerated components of the system are A and B and the only enumerated components of the device are C and D, and further the claim should be interpreted as including equivalents of those components.

A first aspect of the current invention relates to an adult insect cage climate control system 100 comprising a network of any of pipes, liners, conduits, tubes connecting:

a. a local climate control device 106;
b. at least one cluster comprising at least one insect cage 113, 113a-113d, each insect cage 113 comprising a top side 113g, a back side 113h, side walls 113j and 113k, bottom side 113l and front wall 113i and at least one air inlet opening 112, 112a, 112b and at least one air outlet opening 119, 119a-d;
c. optionally an absolute air humidity control unit;
d. a first driver 120b, such as a pump or a fan, for driving temperature controlled and relative air humidity controlled air from the local climate control device 106 to the at least one cluster comprising at least one insect cage 113, 113a-113d, and/or a second driver 122 such as a pump, for pulling or drawing temperature controlled and relative air humidity controlled air from the local climate control device 106 to the at least one cluster comprising at least one insect cage 113, 113a-113d; and
e. at least one air inlet opening 112, 112a, 112b in each of the insect cages 113, 113a-113d, for providing a flow of conditioned air 127 through the insect cages in the direction of the at least one air outlet opening 119, 119a-119d in the cage surface opposite to the air inlet openings, the air outlet openings for transporting conditioned air exiting the insect cages.

For example, the at least one cluster of cages comprises at least two insect cages.

The network of any one or more of pipes comprising at least pipes 103a, 121, 130, 131, 162, 163, 164, 167 connecting the following:

a first pipe 103a connected to the local climate control device 106 for receiving air, wherein the pipe 103a is entering the local climate control device 106 through a first opening connected to a first air temperature control unit 105;

a second pipe 130 connected to the air temperature control unit 105;

optionally a further pipe in fluid connection with second pipe 130 and optionally connecting a relative air humidity control unit;

the second pipe 130 and a fourth pipe 131 in fluid connection with the first driver 120b, such as a pump or a fan, for driving conditioned air, said fourth pipe 131 for transportation of temperature controlled and relative air humidity controlled air from the local climate control device 106 to the at least one cluster comprising at least one insect cage 113, 113a-113d;

the fourth pipe 131 in fluid connection with a fifth pipe 162, said fifth pipe 162 in fluid connection with a sixth pipe 163, said sixth pipe 163 in fluid connection with the at least one air inlet opening 112, 112a, 112b in each of the insect cages 113, 113a-113d, for providing a flow of conditioned air 127 through the insect cages in the direction of the at least one air outlet opening 119, 119a-119d in the cage surface opposite to the air inlet openings; and the air outlet openings in fluid connection with a fifteenth pipe 167, for transporting conditioned air exiting the insect cages.

A second aspect of the current invention relates to an adult insect cage climate control system 100 comprising:
a. a local climate control device 106;
b. at least one cluster of cages comprising at least one insect cage 113, 113a-113d, each insect cage comprising at least one air inlet opening 112, 112a, 112b and at least one air outlet opening 119, 119a-d;
c. a first pipe 103a connected to a first air temperature control unit 105 and connected to the local climate control device 106 for providing the local climate control device 106 with temperature controlled air;
d. a second pipe 130 connected to the first air temperature control unit 105;
e. optionally an absolute air humidity control unit in fluid connection with second pipe 130;
f. a first driver 120b, such as a fan for driving conditioned air, in fluid connection with the second pipe 130 and in fluid connection with a fourth pipe 131, for pushing conditioned air through the insect cage(s), and/or a second driver 122 in fluid connection with the at least one air outlet opening 119, 119a-d, for drawing conditioned air through the insect cage(s). For example, the at least one cluster of cages comprises at least two insect cages. For example, the adult insect cage climate control system comprises the absolute air humidity control unit in fluid connection with second pipe 130. The adult insect cage climate control system is for example configured to controllably provide the at least one cage (113, 113a-113b) with an air flow (127) through the cage(s) with an air temperature of between 25° C. and 38° C.

In one embodiment, the adult insect cage climate control system 100 comprises:
a. a local climate control device 106;
b. at least one cluster comprising at least one insect cage 113, 113a-113d, each insect cage 113, 113a-113d comprising a top side 113g, a back side 113h, side walls 113j and 113k, bottom side 113l and front wall 113i and at least one air inlet opening 112, 112a, 112b and at least one air outlet opening 119, 119a-d;
c. a first pipe 103a connected to a first air temperature control unit 105 and connected to the local climate control device 106 for providing the local climate control device 106 with temperature controlled air;
d. a second pipe 130 connected to the air temperature control unit 105;
e. optionally an absolute air humidity control unit in fluid connection with second pipe 130;
f. a first driver 120b, such as a fan for driving conditioned air, in fluid connection with the second pipe 130 and a fourth pipe 131;
g. the fourth pipe 131 in further fluid connection with a fifth pipe 162, wherein the internal diameter of the fifth pipe 162 is smaller than the internal diameter of the fourth pipe 131, and the fifth pipe 162 in further fluid connection with a sixth pipe 163, wherein the internal diameter of the sixth pipe 163 is smaller than the internal diameter of the fifth pipe 162;
h. the sixth pipe 163 in further fluid connection with the at least one air inlet opening 112, 112a, 112b in each of the insect cages 113, 113a-113d, for providing a flow of conditioned air 127 through the insect cages in the direction of the at least one air outlet opening 119, 119a-119d in the cage surface opposite to the air inlet openings; and
i. the at least one air outlet opening 119, 119a-119d in fluid connection with a fifteenth pipe 167 connected to a seventh pipe 121, for transporting conditioned air exiting the insect cages, the seventh pipe 121 in further fluid connection with an eighth pipe 164, wherein the internal diameter of the eighth pipe 164 is larger than the internal diameter of the seventh pipe 121 and the internal diameter of the seventh pipe 121 is larger than the internal diameter of the fifteenth pipe 167.

In particular, in the adult insect cage climate control system 100 according to the invention,
the fourth pipe 131 is in further fluid connection with a fifth pipe 162, wherein the internal diameter of the fifth pipe 162 is smaller than the internal diameter of the fourth pipe 131, and the fifth pipe 162 in further fluid connection with a sixth pipe 163, wherein the internal diameter of the sixth pipe 163 is smaller than the internal diameter of the fifth pipe 162; and
the sixth pipe 163 in further fluid connection with the at least one air inlet opening 112, 112a, 112b in each of the insect cages 113, 113a-113d, for providing a flow of conditioned air 127 through the insect cages in the direction of the at least one air outlet opening 119, 119a-119d in the cage surface opposite to the air inlet openings.

Alternatively or in addition, the adult insect cage climate control system 100 according to claim 1 or 2, wherein the pipe or pipes connecting second pipe 130 with an air inlet opening 112, 112a, 112b comprise tapered internal diameter with decreasing internal diameter in the direction from second pipe 130 towards air inlet opening 112, 112a, 112b.

It is preferred that the adult insect cage climate control system 100 according to the invention comprises at least one cage 113, wherein the at least one air outlet opening (119, 119a-119d) is in fluid connection with a fifteenth pipe 167 connected to a seventh pipe 121, for transporting conditioned air exiting the insect cages, the seventh pipe 121 in further fluid connection with an eighth pipe 164, wherein the internal diameter of the eighth pipe 164 is larger than the internal diameter of the seventh pipe 121 and the internal diameter of the seventh pipe 121 is larger than the internal diameter of the fifteenth pipe 167.

Additively or alternatively, the adult insect cage climate control system 100 according to the invention comprises a network of pipes, wherein the pipe or pipes connected to an air outlet opening 119, 119a-d of the insect cages 113 comprise tapered internal diameter with increasing internal diameter in the direction from the air outlet opening 119, 119a-d of an insect cage 113, 113a-d towards an proximal end of said connected pipe or pipes.

Preferably, the adult insect cage climate control system 100 according to the invention comprises the first driver 120b for pushing temperature conditioned- and absolute air humidity conditioned air through the at least one cluster of cages.

In addition or alternatively, it is also preferred that the adult insect cage climate control system 100 according to the invention comprises the second driver 122 for pulling temperature conditioned- and absolute air humidity conditioned air through the at least one cluster of cages.

It is particularly preferred that the adult insect cage climate control system 100 according to the invention comprises both the first driver 120b and in addition comprises the second driver 122 for both pushing and pulling temperature conditioned- and absolute air humidity conditioned air from the local climate control device 106 through the at least one cluster of cages each cluster comprising at least one insect cage 113, 113a-d.

It is part of the invention that preferably the adult insect cage climate control system 100 according to the invention comprises at least one insect cage, wherein each insect cage 113 comprises a top side 113g, a back side 113h, side walls 113j and 113k, bottom side 113l and front wall 113i. Thus, encompassing insect cages in the adult insect cage climate control system 100 of the invention, which are closed containers provided with the aforementioned openings, is preferred according to the invention. In particular the adult insect cage climate control system (100, 100a, 1000, 1000a) comprises (a) cage(s), wherein each insect cage (113) comprises a top side (113g), a back side (113h), side walls (113j) and (113k), bottom side (113l) and front wall (113i), wherein preferably the sides and/or walls are impermeable for air and/or for moisture, more preferably the sides and the walls are impermeable for air and for moisture. Such cages protect the interior of the cages, such as a colony of adult insects, e.g. black soldier flies, or insect pupae inside the cage, from (the risk for) contamination.

The inventors found that by applying in the adult insect cage climate control system 100 of the invention connected consecutive pipes or conduits with decreasing internal diameter in the order from larger internal diameter to smaller internal diameter, between driver 120b and the air inlet opening 112, 112a-b of the insect cages, and preferably further applying connected consecutive pipes with increasing internal diameter in the order from smaller internal diameter to larger internal diameter, between the air outlet opening 119, 119a-d of the insect cages and the proximal end of eighth pipe 164, the air flow through all cages within at least one cluster of cages comprising between 1 and about 100 cages, such as about 8 to 64 cages, or 16 to 32 cages, is surprisingly equal. That is to say, with the adult insect cage climate control system 100 of the invention, all of a number of clusters of cages implied in the adult insect cage climate control system 100 of the invention are supplied with essentially the same air flow in m³/hour by the local climate control device 106, and at the individual cluster level, the at least on insect cages 113 in the cluster(s) are supplied with essentially the same air flow, according to the invention. The air flow in an individual cage is stable and independent on the position in e.g. a rack of cages, being the cage at a position closer to driver 120b, or being the cage at a position further away from driver 120b, when cages are arranged in at least one cluster connected through a network of pipes, the pipes in the direction from the driver 120b to air inlet openings 112, 112a, 112b, basically arranged tapered inwardly along the flow path of air. Herewith, the inventors found a surprisingly efficacious method for maintaining the temperature and the absolute air humidity at a stable preset value in all of a number of individual cages, with small to none differences in air temperature and absolute air humidity when cages are compared with neighboring cages in the same cluster or in different clusters, according to the invention. With the application of the adult insect cage climate control system 100 of the invention, the influence of micro climates in a room with insect cages on the temperature inside said cages is minimized.

It is preferred that the adult insect cage climate control system 100 according to the invention further comprises valves 111a-111d, wherein said valves 111a-111d are provided in any of the fourth pipe 131, the fifth pipe 162 or the sixth pipe 163 for controlling transport of conditioned air from the first driver 120b to each of the at least one insect cages 113, 113a-113d comprised by a cluster of cages. For example, the adult insect cage climate control system comprises at least one cluster of cages, each cluster comprising at least two cages.

The adult insect cage climate control system of the invention provides for controlled and stable cage-to-cage air temperature and controlled and stable cage-to-cage air humidity, wherein the temperature window inside the insect cages is surprisingly small, i.e. 2° C. or less, or even 1.5° C. or less, preferably 1° C. or less, as is established by the inventors when assessing temperature control in a plethora of cages positioned at different locations in a farming room, such as the cages located in the top side of a stack of cages compared to the cages closer to the bottom side of the same stack, and when assessing the very same cages throughout an extended period of time over hours to days, and longer. This more steady and homogeneous temperature inside the cages solves the problem of temperature differences when comparing cages for example located near the relatively warm ceiling of a room, in a stack, with cages located near the relatively cool bottom floor of the same room, due to rising warm air, creating a temperature gradient vertically. Furthermore, temperature and absolute air humidity is now controllable at the level of the interior of cages, i.e. for example within at least one cluster of a cluster of a plethora of cages, e.g. 2-500 cages or about 16 to 128 cages such as about 32 to 64 cages, for example clustered in clusters of 4-16 cages or about 64 cages, according to the invention. Up till now, insect cages are temperature controlled and air-humidity controlled at the level of the farming room in which cages are positioned during insect farming, at best. Micro climate differences, i.e. uncontrollable and unnoticed micro climate differences, which occur throughout time of the day and time of the year, throughout a current farming room, impose the aforementioned drawbacks of uncontrollable insect farming timing and results, turnover, yield and product quality, to name a few. Now that the temperature controllable and absolute air humidity controllable cages in the adult insect cage climate control system of the invention has become available by the current inventors, at least one, and in fact several if not all of said aforementioned drawbacks are addressed. Micro climate differences within a cage does not occur anymore, since climate is now controlled at the level of the individual clusters of cages, or at wish, in parallel at the level of several clusters comprising at least one cage each, according to the invention. In addition, also due to the availability now of the adult insect cage climate control system of the invention, climate differences with regard to temperature and absolute air humidity is now also improvingly synchronizable between clusters of cages, throughout a period of time, i.e. during the life cycle of insects at a certain stage of the life cycle, at predetermined values with small deviations therefrom. It is therefore one of the many advantages of the current invention that any influence of presence of micro climates in the direct environment surrounding adult insect cages, on the development of the farmed insects in said cages, is at least reduced to a large extent, if not completely eliminated, by use of the adult insect cage climate control system of the invention. Additionally, by delivery absolute air humidity at the level of individual clusters of cages, each cluster comprising at least one cage and preferably between four and 250 cages, and not anymore at the level of the farming room as is current practice, the inventors forego the need to humidify the air in an entire room, which saves energy proportional to the volume of the cages relative to the volume of the room the cages are placed in. This is a considerable energy and resources saving in an industrial scale room, according to the invention.

Now that closed containers are applied as insect cages in the adult insect cage climate control system of the invention, i.e. at least one adult insect cage comprising side walls, a top wall, a back wall, a front wall and a bottom wall, the insect colony farmed inside the cage is not in open air communication with its environment, i.e. the air surrounding the cage and the room comprising further open insect cages. Such closed containers, i.e. adult insect cages 113, 113a-d, thus provide the important solution to the problem of the risk for contamination of an insect colony with any microbe, which readily occurs with colonies farmed in currently applied open air cages, according to the invention. Furthermore, neighboring insect colonies in closed insect cages do not provide a risk anymore for odor contamination cross cage, due to the application of the closed containers as part of the invention.

In the adult insect cage climate control system 100 according to the invention, the eighth pipe 164 is optionally in fluid connection with a second driver 122 for drawing conditioned air through said eighth pipe 164 connected to the seventh pipe 121 and further to the fifteenth pipe 167, which is in fluid connection with the air outlet opening 119a-d of the individual cages in a cluster of cages.

Preferably, the adult insect cage climate control system 100 according to the invention further comprises an insect farming room climate control device 128 and an insect farming room 115, said insect farming room containing the at least one insect cage 113, 113a-113d comprised by at least one cluster of cages, the insect farming room climate control device 128 comprising a ninth pipe 109 in fluid connection with a second air temperature control unit 161 and a third driver 120a, such as a fan, and the ninth pipe 109 in further fluid connection with air inlet opening 118 of farming room 115 to allow a flow of temperature controlled air 126 into the farming room 115, the farming room 115 further comprising an air outlet opening 117 for connecting the eighth pipe 164 with a tenth pipe 125, for transportation of conditioned air from the farming room 115 outwardly, and said farming room 115 further comprising an air inlet opening 116 for connecting the second pipe 130 with the fourth pipe 131. The insect farming room 115 has side walls 115a, 115b, 115c, 115d, floor 115e and ceiling 115f. The insect farming room encompasses at least one cluster of cages, wherein each one or more cluster(s) comprises at least two insect cages, for example. With the driver 120a a stream of fresh temperature controlled air at the same temperature as the air provided to the at least one cluster comprising at least one cage each by the local climate control device 106, is continuously supplied to the interior of the farming room 115. This way, air inside the farming room is constantly refreshed to a certain extent such that not only the air temperature is stably maintained at the air temperature of the flow of air 127 through each cage, but the air inside the farming room is also continuously cleared from e.g. any excess carbon dioxide present inside the room. Lowering the carbon dioxide throughout farming time to ambient levels is beneficial to the health of workers in the room and reduces the risk for negative effects due to too high levels of carbon dioxide.

It is preferred that the adult insect cage climate control system 100 according to the invention comprises the insect farming room 115, wherein said insect farming room 115 further comprises at least one fan 114a, 114b for homogenizing the air inside the insect farming room. It is part of the invention that any other type of driver configured to mix air to a level of homogeneous air temperature throughout the whole volume of the room, is equally suitable for application in the adult insect cage climate control system 100 of the invention. Such fan 114 further contributes to maintaining the air temperature throughout the farming room at a stable and preset value within a small temperature tolerance, i.e. 2° C. or less, or even 1° C. or less, according to the invention, and such fan 114 aids in removing any noxious gases potentially detrimental to workers in the room such as excess carbon dioxide, from the farming room.

Preferred is the adult insect cage climate control system 100, 100a, 1000, 1000a, wherein the insect farming room 115 further comprises at least one fan 114a, 114b for homogenizing the air, e.g. air temperature, inside the insect farming room 115, wherein the insect farming room 115 comprises at least one first fan 114b configured to horizontally homogenize the air and/or at least one second fan 114a configured to vertically homogenize the air, preferably the insect farming room comprises at least both the at least one first fan 114b and the at least one second fan 114a.

Also preferred is the adult insect cage climate control system 100, 100a, 1000, 1000a, wherein the insect farming room 115 is heat insulated.

In one embodiment, in the adult insect cage climate control system 100 according to the invention, the local climate control device 106 further comprises an air filtering device 107 in fluid connection with the tenth pipe 125 and in fluid connection with an eleventh pipe 124, said eleventh pipe 124 connected to a third air temperature control unit 132, for recirculation of at least part of the conditioned air driven through the insect cages. The filtering device is configured to filter air flown through the cages and optionally also or specifically air flown through the insect farming room, such that the used air is cleared at least partly from one or more of carbon dioxide in excess to a level in air beneficial for the insect farming, ammonia, other gases detrimental to optimal farming conditions. Optionally, the filtering device is alternatively or additively further configured to filter the used air from any particulates such as dust, spores, bits and parts of exuvia, feces, etc. Additively or alternatively, any air inlet opening and/or any air outlet opening is provided with a filter for clearing air entering the insect cage from dust and further particulates, or for clearing used air exiting the insect cage from particulates and/or noxious or otherwise undesired gases when the used air is meant for re-use in the cage climate control device. Furthermore, such a filter in the openings of the insect cage aid in preventing insects such as black soldier flies, farmed inside the cage, from entering the pipes, tubes, conduits, etc., i.e. the network of lines, etc. of the adult insect cage climate control system of the invention.

In a preferred adult insect cage climate control system 100 according to the invention, the system further comprises a central air conditioning unit 101 provided with a twelfth pipe 134 in fluid connection with an air driver device 133 such as a pump, and in fluid connection with an absolute air humidity control unit 108 and a thirteenth pipe 166, said thirteenth pipe 166 in fluid connection with least one air temperature control unit 102a, 102b in fluid connection with the first pipe 103*a*, 103*b*, for driving temperature controlled and absolute air humidity controlled air to at least one local climate control device 106.

Typically, in the adult insect cage climate control system 100 according to the invention, the first pipe 103*a*, 103*b* comprises a valve 104*a*, 104*b* for controlling the flow of temperature controlled and absolute air humidity controlled air from the central air conditioning unit 101 to any of at least one local climate control device 106.

Optionally, the adult insect cage climate control system 100 according to the invention comprises the central air conditioning unit 101, wherein said central air conditioning unit 101 further comprises an air heat exchange device 135 coupled to a fourteenth pipe 165 in fluid connection with the eighth pipe 164, said air heat exchange device 135 configured to allow heat exchange from air driven through the eighth pipe 164 to air drawn into the driver device 133 of the central air conditioning unit 101 through the twelfth pipe 134. As said before, air used in air conditioning of the insect cages is optionally at least in part re-used in the local climate control device 106, once pushed and/or drawn out of the insect cages. Typically, between about 40% and 95% of the circulated air is re-used once exiting the insect cages, preferably about 80% of the air is re-used, preferably after filtering the used air from noxious gases and particulates, if present. In addition, or alternatively, the used air transported by pipes or conduits 167, 121, 164 out of the insect cages is at least in part, and if not re-used in the cage climate control device at all, preferably completely, fed to a controllable heat exchanger 135, which is part of the central air conditioning unit 101 via tubing or pipes connected to driver 122 and to an air inlet opening of the central air conditioning unit 101. In the central air conditioning unit 101, the re-used and relatively warm air is guided along a conduit 134 which transports ambient air into the central air conditioning unit 101, and after heat exchange in the air heat exchange device, into air temperature control unit 102*a-b*. Furthermore, the conduit or pipe 134 for allowing ambient air entering the central air conditioning unit 101 is optionally provided with a filter unit (not shown) for filtering the ambient air entering the adult insect cage climate control system 100 of the invention. Typically, pollen, dust, viruses, moisture, insects, yeast, mold, bacteria, etc., are filtered out of the air drawn into the adult insect cage climate control system 100 by driver 133.

The central air conditioning unit 101 has a modular configuration with regard to the number of local climate control devices 106 that are connectable thereto. The central air conditioning unit 101 is operable when a single local climate control system is connected in fluid connection therewith. Alternatively, the adult insect cage climate control system 100 according to the invention comprises the central air conditioning unit 101, wherein said central air conditioning unit 101 is in fluid connection with between two and hundred local climate control devices 106, preferably three to fifty, such as five to twenty four, or ten, or twenty local climate control systems. Each local climate control device 106, then, is connected to for example 1 to 50 clusters each cluster comprising between one and hundred insect cages. Typically, a local climate control device 106 is connected to about 24 clusters, each cluster comprising between about 8 to 128 insect cages, or between 16 to 64 cages such as about 32 cages. Connecting several local climate control systems to a single central air conditioning unit 101 provides the benefit for improved climate control with regard to uniform and steady preset temperature and with regard to uniform and steady absolute air humidity in any cluster of cages or individual insect cage provided with conditioned air via such local climate control system, when the small deviations in predetermined temperature and/or absolute air humidity are considered on a cluster-to-cluster basis or even at the level of cage-to-cage.

Typically and preferred, in the adult insect cage climate control system 100 according to the invention the central air conditioning unit 101 is in fluid connection with between two and hundred local climate control devices 106.

Typically and preferred, in the adult insect cage climate control system 100 according to the invention the local climate control devices 106 are in fluid connection with between two and 500 insect cages 113, 113*a*-113*d* preferably between 8 and 128 cages, more preferably between 16 and 96 cages, most preferably between 32 and 64 cages. In fact, due to the flexible lay out of the network of pipes, conduits, liners, tubings, etc., connecting the elements of the adult insect cage climate control system, any desired number of insect cages is incorporated in the air conditioning system, wherein the capacity of conditioned air from an air volume per hour perspective is adjustable by implementing an enlarged local climate control system and/or by implementing additional local climate control systems in the network.

The adult insect cage climate control system 100 according to the invention is preferably configured to maintain the air temperature inside the at least one cage 113, 113*a*-113*d* within a temperature range of 2° C. or less, preferably 1° C. or less, such as within a temperature range of 0.05° C.-0.5° C. Temperature inside the individual insect cages is controlled by the controllable valves 111*a-d* in the network of pipes, conduits, etc., the driver 120*b* and the air temperature control units 102*a*, 102*b*, 105, 132, 161. That is to say, control units provide the possibility to adjust the speed and/or volume of the air flow delivered at a cage through air inlet opening 112, to adjust the air temperature, and to even deprive a selected insect cage completely, temporarily, by blocking the flow of conditioned air to a selected cage. In addition, the cage climate control device is controllable as to cool cages at the cluster level or at the individual cage level, according to the invention, if individual cages or an individual cluster of cages are each separately coupled locally to an air temperature control unit and a driver, according to the invention. Importantly, due to the application of pipes, tubes, conduits, liners having pipe-to-pipe variable internal diameters as here above outlined for pipes 131, 162, 163, 167, 121 and 164, it is now possible due to the invention to supply each of any number of clusters of at least one cages, e.g. 32 to 128 cages, with a flow of conditioned air at essentially the same velocity in cubic meter air per hour, said air being temperature conditioned and being absolute air humidity conditioned as the result of the application of the local climate control devices 106 and typically also due to the presence of the insect farming room climate control device 128 and farming room 115.

Typically, the adult insect cage climate control system 100 according to the is configured to controllably provide the at least one cage 113, 113*a*-113*d* with an air flow 127 through the cage(s) of between 10 m$^3$/hour and 200 m$^3$/hour, preferably about 100 m$^3$/hour, more preferably about 45 m$^3$/hour. Such volumes of conditioned air provided to the insect cages are sufficient and enough to control temperature and absolute air humidity inside said cages within the desired narrow temperature window of e.g. 1.5° C. or less, and to maintain absolute air humidity at a preset value. In addition, air flows of between 10 m$^3$/hour and 200 m$^3$/hour through the cages efficaciously removes any harmful gases present and produced inside the cages, in order to facilitate and maintain a healthy environment for the pupae, adult insects and deposited eggs. Typically, the adult insect cage climate control system comprises at least one cluster of cages, wherein each cluster comprises at least two cages, such as 2-100 cages, or 3-36 cages, or 4-32 cages, or 5-25 cages, or 8-24 cages, such as 10, 12, 16, 20 cages.

For example, for optimal insect colony development, timing and speed and synchronization of hatching of all pupae present in an insect cage, facilitating optimal conditions for development and mating and ovipositioning of the adult flies, and optimally synchronize ovipositioning by gravid female flies and to optimally preserve eggs, the adult insect cage climate control system 100 according to the invention is configured to controllably provide the at least one cage 113, 113a-113d with an air flow 127 through the cage with a temperature of between 25° C. and 38° C., preferably between 28° C. and 35° C. For example, the adult insect cage climate control system is configured to controllably provide the at least two cages 113, 113a-113d with an air flow 127 through the cages with an air temperature of between 28° C. and 35° C., preferably between 29° C. and 34° C., more preferably between 30° C. and 33.5° C., most preferably between 31° C. and 33° C. As indicated before, it is now due to the invention that such a preset temperature of the conditioned air provided to the insect cages is maintained in time and when considering different cages, within a narrow temperature window of 2.5° C. or less, or even 1.2-0.7° C. or less. Optimization of the insect farming is thus both facilitated by the ability to steadily maintain a predetermined temperature at the level of the individual cage or individual cluster of cages, and the ability to maintain the temperature within a small window, due to the application of the adult insect cage climate control system of the invention.

Preferably, the adult insect cage climate control system 100 according to the invention is configured to maintain the air temperature inside the insect farming room 115 within a temperature range of 2° C. or less, preferably 1° C. or less, such as within a temperature range of 0.05° C.-0.5° C. Preferably, the temperature within a cage is kept within a temperature window of plus/minus 1° C. or less, more preferably about plus/minus 0.3° C. to 0.8° C. or less such as 0.5° C. or less. For example, applying the adult insect cage climate control system of the invention results in a steady and constant temperature within each cage and when compared different cages, wherein the temperature is for example between 30° C. and 31° C., or is about 33.5° C. plus/minus 0.6° C. or less, according to the invention. With such surprisingly small temperature difference on a cluster of cages to cluster of cages basis and even on a cage-to-cage basis and throughout a period of farming time, e.g. the time an insect colony is bred in a cage, the insect farming becomes improvingly predictable and controllable. Insect farming in separate cages, in parallel or consecutively, or in the same cages consecutively, provides a more homogeneous end product with regard to for example the number and quality of insect eggs, deposited at desired locations inside the cages, and with regard to for example the time point at which gravid female insects start laying eggs, end laying eggs, and the duration of the period in which a number of gravid female insects lay eggs within a cage. In addition, emergence of adult insects from pupae provided to such a tight temperature controlled cage is improvingly synchronizeable within a batch of insect pupae and when different cages comprising pupae are considered, due to the benefits of the current invention. Moreover, tight temperature control also provides for timing and tuning the occurrence of a process within the insect life cycle on a cage-to-cage basis. That is to say, for example within a farming room provided with clusters or batches of for example 4 to 16 adult insect cages, the hatching of adult insects from pupae provided to these cages is controllable with the adult insect cage climate control system of the invention on the level of clusters of cages and/or on the level of individual cages, according to the invention. This way, for example by controlling temperature in clusters of cages differently, the time at which pupae in separate cages hatch may vary at wish, and/or the time window in which adult insects mate, and/or gravid female insects lay eggs, may vary. Further, it is now due to the provision of the adult insect cage climate control system of the invention that also for example clusters of cages or individual cages within a cluster of cages, are/is temporarily not warmed with temperature controlled air from the adult insect cage climate control system of the invention, or is even cooled, at wish, for example when the cage(s) are idle, i.e. do not comprise a colony of insects.

It is further preferred that the adult insect cage climate control system 100 according to the invention is configured to controllably provide the insect farming room 115 with an air flow 126 through the insect farming room with a temperature of between 25° C. and 38° C., preferably between 28° C. and 35° C., more preferably between 29° C. and 34° C., most preferably between 31° C. and 33° C. Together with the application of at least one fan 114a, 114b in the insect farming room, the insect farming room climate control device 128 of the adult insect cage climate control system of the invention, provides for a improvingly stable temperature inside the insect farming room, and thus the air surrounding the exterior of insect cages inside the room is maintained at a predetermined temperature, which is the same temperature within a smaller window, as the temperature inside the cage. This way, maintaining the temperature inside the cage steadily at a predetermined value has now become possible, since with the application of the insect farming room climate control device 128 together with the fans 114a, 114b, presence of micro climates inside the insect farming room is largely reduced, if not excluded completely, compared to current farming rooms. The better the climate of the insect farming room is controlled and stabilized with the use of the adult insect cage climate control system of the invention, the better the climate inside the cages is stabilized due to the use of the very same adult insect cage climate control system of the invention. Although possible, the insect farming room climate control device 128 is not necessarily configured to stabilize and maintain a preset value for the absolute air humidity of the air provided to the insect farming room. Since the insect cages are closed containers according to a preferred embodiment of the invention, the climate inside the cages is shielded from the climate outside the cages, e.g. in the insect climate room. The temperature outside the cages has an influence on the temperature inside the cages in the sense that the local climate control device 106 of the adult insect cage climate control system of the invention controllably flows an amount of conditioned air through the cages in order to keep the temperature inside the cages stable and at a preset value.

Particularly, in the adult insect cage climate control system 100 according to the invention, the relative air humidity control unit 108 is preferably configured to controllably provide the at least one cage 113, 113a-113d with an air flow 127 through the cage with an absolute air humidity of between 5 gram $H_2O$/kg air and 46 gram $H_2O$/kg air at an air temperature of between 25° C. and 38° C. at atmospheric pressure of 1.0 bar, preferably an absolute air humidity of between 10 gram $H_2O$/kg air and 30 gram $H_2O$/kg air at an air temperature of between 28° C. and 35° C. at atmospheric pressure of 1.0 bar. Preferred is the adult insect cage climate control system 100, 100a, 1000, 1000a, wherein the absolute air humidity control unit 108 is configured to controllably provide the at least two cages 113, 113a-113d with an air flow 127 through the cages with an absolute air humidity of between 5 gram $H_2O$/kg air and 46 gram $H_2O$/kg air at an air temperature of between 25° C. and 38° C. at atmospheric pressure of 1.0 bar, preferably an absolute air humidity of between 10 gram $H_2O$/kg air and 30 gram $H_2O$/kg air at an air temperature of between 28° C. and 35° C., preferably between 29° C. and 34° C., more preferably between 31° C. and 33° C., at atmospheric pressure of 1.0 bar. It has been established that the processes occurring in the insect cages with regard to the incubation of pupae, e.g. of black soldier fly, the hatching of said pupae, the development of the adult flies, the facilitation of the mating process and finally the ovipositioning by the gravid female flies and the preservation of the laid eggs in order to be able to optimally reap the precious eggs, are beneficially supported by the adult insect cage climate control system of the invention, if said control system enables a conditioned air flow through said cages, the conditioned are comprising an amount of water vapor relating to absolute air humidity of between 5 gram $H_2O$/kg air and 46 gram $H_2O$/kg air at an air temperature of between 25° C. and 38° C. at atmospheric pressure of 1.0 bar, preferably an absolute air humidity of between 10 gram $H_2O$/kg air and 30 gram $H_2O$/kg air at an air temperature of between 28° C. and 35° C. at atmospheric pressure of 1.0 bar, according to the invention. The absolute air humidity is under control of the controllable air humidity control unit 108 for controlling the air humidity of the stream of air provided by the central air conditioning unit 101 to the local climate control device 106.

Since the adult insect cage climate control system of the invention provides conditioned air at the individual cluster of cages level to the insect cages, which are closed containers not in open communication with the air in the environment, e.g. the farming room according to the invention, the interior of the insect cages is conditioned at a steady controllable predetermined and preset absolute air humidity within the range of between 5 gram $H_2O$/kg air and 46 gram $H_2O$/kg air at an air temperature of between 25° C. and 38° C. at atmospheric pressure of 1.0 bar, preferably an absolute air humidity of between 10 gram $H_2O$/kg air and 30 gram $H_2O$/kg air at an air temperature of between 28° C. and 35° C. at atmospheric pressure of 1.0 bar, according to the invention, since the relative air humidity control unit 108 is configured to controllably provide the at least one cage 113, 113a-113d with an air flow 127 through the cage with such an absolute air humidity. Thus, this way, cages at the cluster level have contained and stable absolute air humidity in their interior. Due to the insects cages being closed containers without open air communication, less effort in terms of energy for operating drivers and less humid air is required to maintain the absolute air humidity inside the cages within a predetermined range, since humid air cannot escape the interior of the cage through e.g. an open top side or the like.

Furthermore, air leakage out of the insect cages, as seen with current open sided or open topped cages in the art, is undesirable because in general such air leakage tends to create temperature heterogeneity in the cage, and humidity heterogeneity, which negatively affects in-cage fly conditions. Homogeneous and controlled predetermined in-cage fly conditions are important and contribute to efficacious insect farming. Without wishing to be bound by theory, it is known in the art that male flies stake out a position in the cage to spot mates from. Males who stake out a suboptimal spot in the cage will be disadvantaged by a climate that weakens them, even if they otherwise have good genetics. An even climate provides an even ground for genetics to compete on factors other than luck and chance. Thus providing the interior of the insect cages with a homogenous climate with regard to temperature and absolute air humidity according to the invention is valuable for mass breeding for desirable genetic strains.

It is preferred that in the adult insect cage climate control system 100 according to the invention, the at least one cage 113, 113a-113d or the at least two cages is/are a heat insulated cage. Heat insulation of the cages is for example established by covering the exterior of the cage with an insulation cover such as a film of insulating material, for example laminar films enclosing e.g. a layer of air, glass wool, cardboard honeycomb structure, etc., known in the art. A preferred heat insulation is providing the exterior of the insect cages with a layer of foam material, e.g. a layer with a thickness of between 8 mm and 20 mm foam, such as rigid PIR, PUR or phenolic foam known in the art. Heat insulation of the cages supports the climate control and supports the stability of the cage climate with regard to temperature and absolute air humidity inside the cages, and with regard to maintaining temperature and absolute air humidity inside the cages within a desired small window of values. Influences of temperature and temperature differences present in the environment surrounding cages, are reduced by heat insulation of the cages. Of course, heat insulation of cages is energy saving, since losses of warm air, or cool air, as the case may be, from the interior of the cages outwardly is reduced upon applying heat insulation. Preferably, also the pipes, conduits, liners, tubes of the adult insect cage climate control system 100 of the invention are insulated. For example, for the adult insect cage climate control system 100, 100a, 1000, 1000a, any one or more of the pipes is/are heat insulated, preferably all pipes are heat insulated. An example is the adult insect cage climate control system 100, 100a, 1000, 1000a wherein any one or more of the first pipe 103a, second pipe 130, fourth pipe 131, fifth pipe 162, sixth pipe 163, ninth pipe 109 and thirteenth pipe 166 is heat insulated, preferably all said first pipe 103a, second pipe 130, fourth pipe 131, fifth pipe 162, sixth pipe 163, ninth pipe 109 and thirteenth pipe 166 are heat insulated. Optionally, in the adult insect cage climate control system 100 according to the invention, the at least one cage or the two or more cages 113, 113a-113d is/are a cage comprising rounded corners at least at the interior side. In one embodiment, in the adult insect cage climate control system 100 according to the invention, the at least one cage 113, 113a-113d is arranged to have round corners in the inner surface of the cage. According to the invention, a smooth interior of the cages contributes to unencumbered air flow inside the cages from the location of the air inlet in the direction of the cage air outlet throughout the whole volume of the interior of the cage. This way, the rounded corners contribute to the smoothness of the interior surface of the cage, and therewith contribute to optimal airflow through the cage and stable and constant temperature and stable and constant absolute air humidity throughout the whole cage. The cluster or clusters of cages each comprise for example two or more cages.

The adult insect cage climate control system 100 according to the invention comprises at least one cage, the at least one cage 113, 113a-113d preferably being a blow molded cage or a rotation molded cage made of a polymer or polymer blend. Molding of a polymer or polymer blend provides for a cage having a relative smooth surface at the interior. As said before, a smooth surface inside the cage contributes to optimal mixing and flow of temperature conditioned and air humidity conditioned air throughout the whole inner volume of the cage. Of course, other conventional methods for manufacturing smooth-surfaced cages known in the art are equally applicable, according to the invention.

In an exemplary adult insect cage climate control system 100 according to the invention, the at least one cage 113, 113a-113d is made of polypropylene or polyethylene. Cages made of for example medium density polyethylene are particularly suitable for implication in the adult insect cage climate control system of the invention, since for example blow molding or rotation molding of polyethylene provides for suitably smooth surfaced insect cages.

Particularly, in the adult insect cage climate control system 100 according to the invention, the at least one cage 113, 113a-113d has inner dimensions of a width between 30 cm and 150 cm, a depth between 50 cm and 200 cm and a height between 10 cm and 60 cm, preferably a width of about 100 cm, a depth of about 170 cm and a height of about 50 cm, and more preferably a width of about 90 cm, a depth of about 140 cm and a height of about 40 cm. Insect cages having such dimensions are particularly compatible with the air flow volumes indicated here above, with regard to maintaining the temperature within the narrow range of temperatures according to the invention. For example, the two or more cages comprised by the adult insect cage climate control system 100, 100a, 1000, 1000a, have inner dimensions of a width between 15 cm and 200 cm, a depth between 30 cm and 300 cm and a height between 5 cm and 100 cm, preferably a width between 30 cm and 150 cm, a depth between 50 cm and 200 cm and a height between 10 cm and 60 cm, more preferably a width of about 100 cm, a depth of about 170 cm and a height of about 50 cm, and most preferably a width of about 90 cm, a depth of about 140 cm and a height of about 40 cm.

It is due to the specific arrangement of pipes or conduits in inwardly tapered fashion from driver 120b of the local climate control device 106 in the direction of the at least one cluster of cages, that each insect cage in the cluster(s) receives conditioned air which is essentially the same when compared to the conditioned air in neighboring cages in a cluster, or when clusters of cages are compared, with regard to stable temperature within a small range and with regard to absolute air humidity.

For example, in the adult insect cage climate control system 100 according to the invention, the second pipe 130 has an internal diameter of between 100 mm and 400 mm, preferably between 150 mm and 300 mm, such as about 200 mm.

For example, in the adult insect cage climate control system 100 according to the invention, the fourth pipe 131 has an internal diameter of between 125 mm and 500 mm, preferably between 175 mm and 400 mm, such as about 250 mm.

For example, in the adult insect cage climate control system 100 according to the invention, the fifth pipe 162 has an internal diameter of between 80 mm and 320 mm, preferably between 120 mm and 200 mm, such as about 160 mm.

For example, in the adult insect cage climate control system 100 according to the invention, the sixth pipe 163 has an internal diameter of between 40 mm and 160 mm, preferably between about 60 and 120 mm, such as about 80 mm.

The inventors now found that arranging the pipes and conduits between the temperature control unit 105 and air inlet openings 112, 112a, 112b in a specific manner, e.g. with the fourth pipe 131 having an internal diameter of about 220 mm to 270 mm, connected to the fifth pipe 162, having an internal diameter of between 140 mm and 185 mm, the fifth pipe connected to the sixth pipe 163, having an internal diameter of between 65 mm and 100 mm, the flow of conditioned air between driver 120b and air inlet openings 112, 112a-b in the insect cages is preferably 2 m/s to 10 m/s in fourth pipe 131, 1.5 m/s to 8 m/s in fifth pipe 162, 1 m/s to 5 m/s in sixth pipe 163 and 1.2 m/s to 6 m/s in second pipe 130 connected to the air inlet side of driver 120b, such that in all the insect cages 113 of for example a single cluster of about 16 cages, the flow of conditioned air 127 is about 30 $m^3$/hour to 70 $m^3$/hour, preferably about 40 $m^3$/hour to 50 $m^3$/hour, and desirably about 45 $m^3$/hour. The inventors established that by application of the indicated pipe diameters in the consecutive order as indicated, the flow of conditioned air through all locations of the network of pipes was sufficient and adequate for providing all cages in the cluster with the same flow of conditioned air 127 through the individual cages. Herewith, temperature is not only constant within a single cage within a desired period of time, but also when temperature at the cage-to-cage level is assessed with regard to the absolute value, which is stable, and with regard to fluctuations during a period of time, which is hardly to not occurring due to the invention.

Preferably, in the adult insect cage climate control system 100 according to the invention, the fifteenth pipe 167 has an internal diameter of between 45 mm and 180 mm, preferably between 65 mm and 150 mm, such as about 90 mm.

For example, in the adult insect cage climate control system 100 according to the invention, the seventh pipe 121 has an internal diameter of between 80 mm and 320 mm, preferably between 120 mm and 210 mm, such as about 160 mm.

Preferably, in the adult insect cage climate control system 100 according to the invention, the eighth pipe 164 has an internal diameter of between 100 mm and 400 mm, preferably between 160 mm and 280 mm, such as about 200 mm.

As said, arranging conduits inwardly tapering with regard to the internal diameter in the order from a first conduit connected to driver 120b having the relatively largest internal diameter, a second conduit in fluid connection with the first conduit, having a smaller internal diameter, etc., up to the conduit connected to the insect cage, having the smallest internal diameter, flow of temperature controlled and absolute air humidity controlled air through the individual cages is such that air temperature and absolute air humidity are stably maintained at a preset value at the level of temperature control unit 105 and at the level of air humidifier 108, within each cage and when cages are compared, wherein the position of said cages in a farming room and in a cluster network of cages is not influencing temperature and air humidity in the cage. Furthermore, the selection of the conduits with decreasing internal diameter when considering said internal diameter, is crucial for obtaining the cage-to-cage stability with regard to air humidity and temperature, i.e. for arriving at a constant air flow 127 of about 25 $m^3$/hour to 70 $m^3$/hour, through each and every cage within a cluster of cages and when cages present in different clusters of cages provided with conditioned air in parallel from the same local climate control device 106, or even when comparing cages located in different clusters of cages supplied by conditioned air from different local climate control devices 106 connected to the same or different central air conditioning units 101. Stable temperature and stable absolute air humidity in a cage throughout farming time and when considering different cages in a cluster and different cages in different clusters, was further satisfactorily supported with the adult insect cage climate control system 100 of the invention, when for example fifteenth conduit 167 had a diameter of between 70 mm and 120 mm, such as about 90 mm, the seventh conduit 121 connected thereto had a diameter of between 135 mm and 180 mm, such as about 160 mm, the eighth conduit 164 connected to the seventh conduit 121 had a diameter of between 180 mm and 240 mm, such as about 200 mm. Of course it is particularly preferred to combine the pipes with inward taper when consecutively coupled, as here above described, with the pipes with outward taper when consecutively coupled, wherein the line of inwardly tapered pipe elements is in fluid connection with the air inlet opening of the cage, with the conduit having the largest diameter connected to the air inlet of the cage, and the line of outwardly tapered pipe elements is connected with the air outlet opening of the cage, with the conduit having the smallest diameter connected to the air outlet of the cage. In a typical example of a network of pipes contributing to transporting a flow of conditioned air through the various elements of the adult insect cage climate control system 100 of the invention, pipe 130 of the local climate control device 106 is arranged to provide an air flow to driver 120b, the driver being a fan, of preferably about between 2.5 m/s and 3 m/s; fourth pipe 131 has an internal diameter of about 250 mm, allowing a flow of between 4 m/s and 5 m/s; fifth pipe 162 has an internal diameter of between 3 m/s tot 4 m/s; and sixth pipe 163 has an internal diameter of between 2 m/s tot 2.5 m/s, according to the invention. It is preferred that fifteenth pipe 167 has a diameter of about 90 mm, allowing a flow of air from the interior of the cage outwardly of about 2 m/s to 2.5 m/s; seventh pipe 121 has a diameter of about 160 mm allowing an air flow of between 3 m/s and 4 m/s; and the eighth pipe 164 has a diameter of about 200 mm allowing an airflow of between 4 m/s to 5 m/s. With such a network of pipes connected to a cluster or multiple clusters of between 20 and 100 cages, the flow of conditioned air in the adult insect cage climate control system 100 of the invention is in the preferred range of 15 $m^3$/hour to 135 $m^3$/hour, preferably 45 $m^3$/hour, in order to avoid temperature heterogeneity and to avoid fluctuations in absolute air humidity within cages and when comparing different cages. It will be appreciated by the person having ordinary skills in the art, that of course the same beneficial effects on in-cage and cage-to-cage temperature and air humidity stability throughout time is achievable when connecting a different number of tubes than three with declining internal diameter from fan 120b to the air inlet 112 and/or with increasing internal diameter from the air outlet opening 119 and further. For example, the same temperature stability in the cage is established when four or five tubes having declining internal diameter are coupled to each other and then to the air inlet opening 112. Therefore, the invention is not limited to the embodiments here described.

In addition, the inventors found that providing the adult insect cage climate control system 100 of the invention with consecutive conduits connected to the air outlet opening of the cages 112, wherein said consecutive conduits are tapered outwardly with regard to their internal diameter in the direction of the air outlet opening towards driver 122 for drawing air through eighth pipe 164, further contributes to maintaining the air temperature inside the cages and maintaining the absolute air humidity inside the cages at a desired and preset value, controlled by e.g. controllers 108, 102a, 105.

The adult insect cage climate control system 100 according to the invention comprises in preferred embodiments the insect farming room 115, wherein the size of said insect farming room 115 is 5 meter to 100 meter (width), 10 meter to 150 meter (length), 2 meter to 20 meter (height), preferably 8 meter to 40 meter (width), 15 meter to 75 meter (length), 3 meter to 8 meter (height).

Optionally, the adult insect cage climate control system 100 according to the invention comprises the insect farming room 115, wherein said insect farming room 115 is provided with an air outlet opening in a side wall in fluid connection with a further pipe, the further pipe in fluid connection with second air temperature control unit 132 and pipe 130 of the local climate control device 106, such that the stream of conditioned air 126 is at least partly recyclable by the local climate control device 106.

The above embodiments are to be understood as illustrative examples of the invention. It is to be understood that any feature described in relation to any one embodiment may be used alone, or in combination with other features described, and may also be used in combination with one or more features of any other of the embodiments, or any combination of any other of the embodiments, in so far not indicated otherwise. Furthermore, equivalents and modifications not described above may also be employed without departing from the scope of the invention, which is defined in the accompanying claims and their equivalents.

DEFINITIONS

The term "air" has its regular scientific meaning and here refers to the air surrounding the earth at ground level.

The term "ambient" has its regular scientific meaning and here refers to that what is surrounding something. Ambient air thus refers to the air surrounding an object such as a farming room, an insect cage, an air conditioning system or device, etc.

The term "insect" has its regular scientific meaning and here refers to all stages of an insect, e.g. pupae, adult insect, neonate larvae, larvae, prepupae.

The term "conditioned" has its regular scientific meaning and here refers to a gas, as in conditioned gas such as ambient air, with preset values for predetermined parameters such as the temperature of air or the water content of air at a set temperature, within a certain tolerance.

The term "absolute air humidity" has its regular scientific meaning and refers to the water content of air expressed in $gr/m^3$ or gr/kg.

The term "relative air humidity" has its regular scientific meaning and refers to the current absolute air humidity at the current temperature relative to the maximum air humidity (highest point) for that temperature, expressed as a percentage.

BRIEF DESCRIPTION OF THE DRAWING

FIG. 2 outlines an adult insect cage climate control system 100a.

DETAILED DESCRIPTION OF PREFERRED EMBODIMENTS

Figure 1:
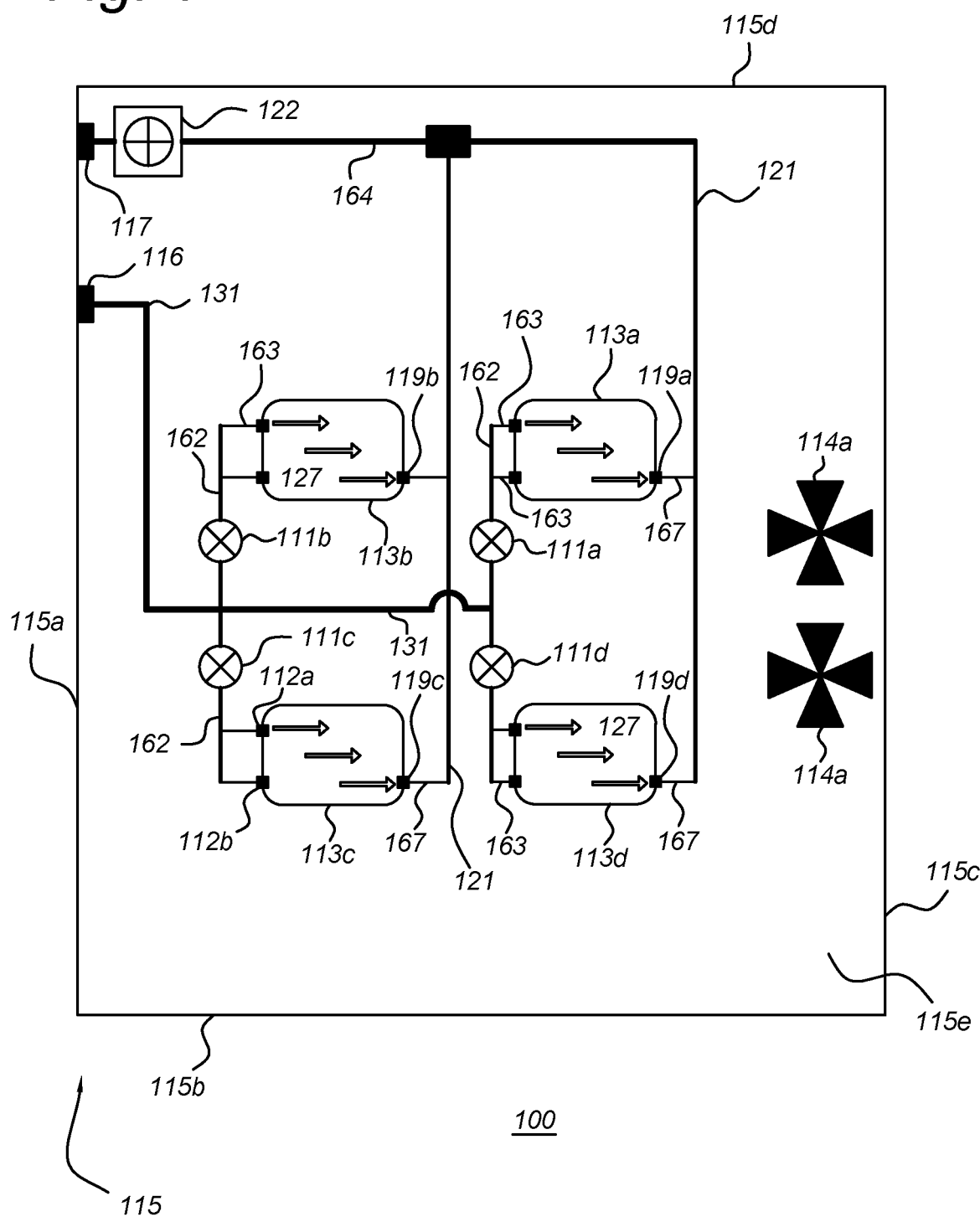
In FIG. 1, a preferred embodiment of an insect farm climate control system 100, or an adult insect cage climate control system 100, of the invention is outlined.

Reference is made to the drawings in FIG. 1-5. An insect farm climate control system 1000 comprises a central air conditioning unit 101 provided with an air driver device 133 such as a pump, and with air temperature control units 102a and 102b (See FIG. 3). The temperature control unit 102a of the insect farm climate control system is coupled with a connector and pipes and/or tubes 103a with local climate control device 106 (FIG. 1, FIG. 2; insect farm climate control system 100a). Local climate control device 106 is optionally provided with a controller, wherein the controller can switch the climate control device from an off state to an operation state. The pipes and/or tubes 103a are provided with valve 104a, which valve is optionally provided with a controller, said controller configured to switch the valve from an open state to a closed state, and vice versa.

The central air conditioning unit 101 is optionally further provided with pipes and/or tubes 103b comprising valve 104b, which is also optionally connected to a controller, via temperature control unit 102b, which is also optionally connected to a controller, for coupling the central air conditioning unit 101 with a further local climate control system (not shown).

According to the invention, the central air conditioning unit 101 is optionally further provided with one or more pipes and/or tubes, lines, conduits, via one or more further temperature control units, for coupling the central air conditioning unit 101 with one or more further local climate control systems (not shown).

The pipes and/or tubes 103a are coupled with a coupler to a temperature control unit 105, of the local climate control device 106, for controlling the air temperature of the air flowing from the central air conditioning unit 101 into the pipes and/or tubing 130 of the local climate control device 106.

The farming room climate control device 128 (See FIG. 3A; insect farm climate control system 1000) comprises optionally a controller, and further comprises tubes and/or pipes 109 provided with a driver 120a such as a pump or fan (see FIG. 3A), said driver optionally provided with a controller for switching the e.g. fan to an off state when in operation, or vice versa. The farming room climate control device further comprises air temperature control unit 161. The tubes and/or pipes 109 connect the farming room climate control device with farming room 115 (See FIG. 1; insect farm climate control system 100; See FIG. 2; insect farm climate control system 100a: See FIG. 3A; insect farm climate control system 1000) for breeding insect pupae and adult insects in at least one adult insect cage 113, 113a-d (FIGS. 1, 2, 3A, 4, 5) comprised by at least one cluster of adult insect cages, said at least one cluster comprised by the insect farm climate control system 100, 100a, 1000, 1000a of the invention, at the conditioned air inlet opening 118 of the farming room 115. Farming room 115 has side walls 115a, 115b, 115c, 115d, and has floor 115e, and has ceiling 115f (See also FIG. 3B; insect farm climate control system 1000a). Driver 120a provides for a stream of conditioned air 126 which is temperature controlled. Fans 114a, 114b inside the farming room contribute to homogeneous spreading and constant circulation of the incoming conditioned air, such that the interior of the farming room has a homogeneous air temperature. These fans 114a are optionally provided with a controller, which can switch between various states, wherein the rotational speed of the fans depends on a selected state of the controller.

The local climate control device 106 further is provided with pipes and/or tubings 130 optionally connected to the tubing and outlet of an air humidity control unit (not shown) for controlling the air humidity of the stream of air provided by the central air conditioning unit 101 to the local climate control device 106.

Figure 2:
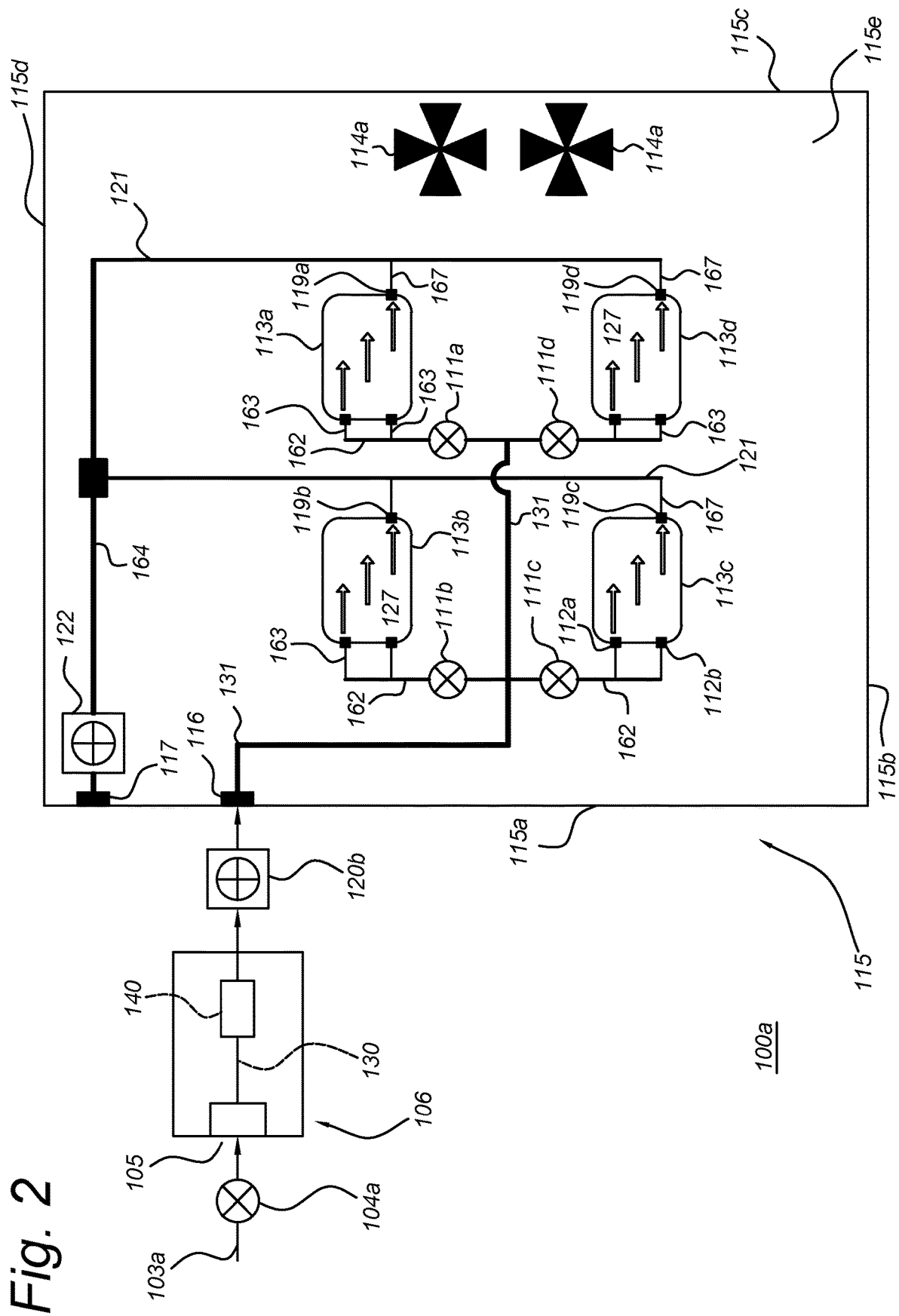
Figure 3A:
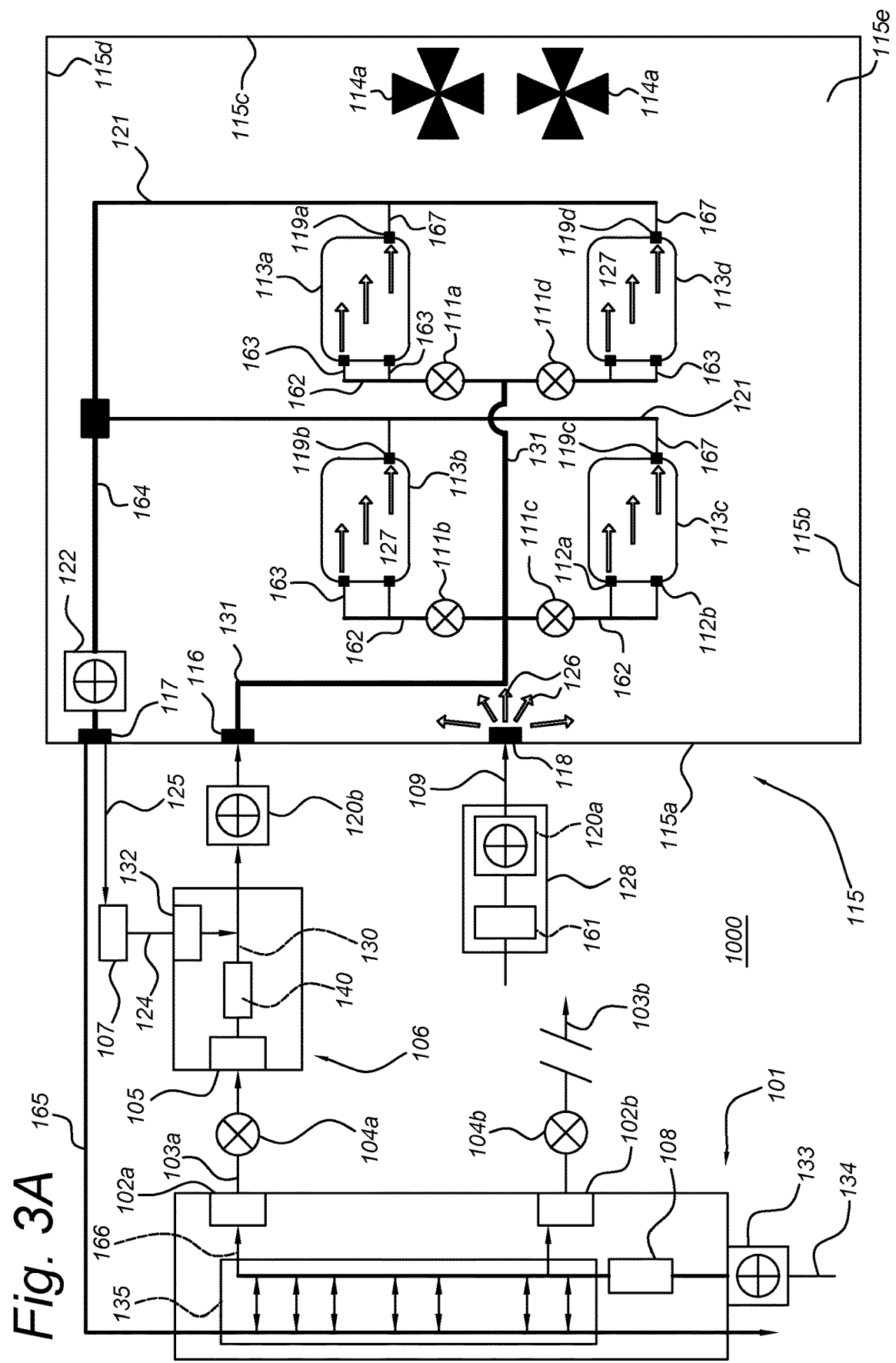
FIG. 3A and FIG. 3B outline an adult insect cage climate control system 1000 and an adult insect cage climate control system 1000a, respectively.

The local climate control device 106 is coupled to a driver 120b through the tubes and/or pipes 130 (FIG. 3A), said driver, such as a pump, arranged to drive temperature controlled and air humidity controlled air to at least one cluster of at least one cage 113, 113a-d for insect farming (FIGS. 1-3). In some embodiments, the local climate control device 106 of the invention is coupled to a driver 120b through the tubes and/or pipes 130, said driver, such as a fan, arranged to drive temperature controlled and air humidity controlled air to farming room 115 (FIG. 3A), i.e. to conditioned air inlet opening 116 of the farming room 115.

Turning to FIGS. 1, 2 and 3A, pipes 131 provided with valves 111a-111d to allow transport of temperature controlled and air humidity controlled air from driver 120b to any one or more of the adult insect cages 113a-113d, e.g. inside the farming room 115, the cages connected to the valves via pipes 162 and coupling pipes 163.

Adult insect cages 113a-113d each are provided with couplers and inlet openings 112, 112a and 112b (FIGS. 1, 2, 3A, 4 and 5), for coupling pipes 163 with the adult insect cages such that the temperature controlled and air humidity controlled air can be driven into any one or more of the adult insect cages, i.e. under control of valves 111a-111d.

When temperature controlled and air humidity controlled air is provided to an adult insect cage, an air stream 127 from the air inlet openings 112, 112a and 112b towards an air outlet opening 119, 119a-119d is established.

The air outlet openings 119, 119a-119d of the insect cages are provided with a coupler (not shown), coupled to pipes 167, and further coupled to pipes 121 for further transport of temperature controlled and air humidity controlled air exiting the cages, in some embodiments said air exiting the cages is transported out of the farming room 115 through an air outlet opening 117 of the farming room 115 (FIG. 3A). Pipes 164 are optionally provided with a pump 122 configured for drawing the air out of the adult insect cages 113, 113a-d through openings 119, 119a-119d.

The air exiting the insect cages, and in some embodiments thereafter exiting the farming room 115 through air outlet opening 117, is optionally at least partly introduced into an air filtering unit 107 (FIG. 3A), which is coupled to the air outlet opening 117 with line 125, and is configured to filter air from any particulates, viruses, dust, mold, superfluous moisture, excess amounts of gases such as carbon dioxide in excess to the level of carbon dioxide in ambient air, waste gases excreted by pupae and/or adult insects and/or insect eggs produced by the gravid female insects, olfactory attractant, ammonia, etc., said filtering unit coupled through pipe 124 with a temperature control unit 132 of the local climate control device 106, such that the filtered air is reintroduced in the local climate control device 106 for reuse purposes (FIG. 3A).

FIG. 3A further outlines embodiments of the climate control system of the invention, comprising the central air conditioning unit 101 provided with an air driver device 133 such as a pump, and with air temperature control units 102a and 102b. The temperature control unit 102a of the insect farm climate control system is coupled with a connector and pipes and/or tubes 103a with local climate control device 106, and further a farming room climate control device 128 is provided in this embodiment. The pipes and/or tubes 103a are provided with valve 104a. The central air conditioning unit 101 is further provided with heat exchange unit 135 configured for heat exchange between relatively warm air in pipes/tubes 165 exiting the cages 113a-d and air at ambient temperature drawn in the central air conditioning unit 101 through pipe 134. In addition, the central air conditioning unit 101 is provided with air humidity control unit 108. The conditioned air exiting the heat exchange unit 135 is transportable to air temperature control units 102a, 102b through pipes 166 connecting the air temperature control units and the heat exchange unit.

The central air conditioning unit 101 is optionally further provided with one or more pipes and/or tubes 103b comprising valve 104b, via temperature control unit 102b, for coupling the central air conditioning unit 101 with a further local climate control system (not shown).

According to the invention, the central air conditioning unit 101 is optionally further provided with one or more pipes and/or tubes via one or more further temperature control units, for coupling the central air conditioning unit 101 with one or more further local climate control systems (not shown).

The pipes and/or tubes 103a are coupled with a coupler to the temperature control unit 105 of the local climate control device 106, for controlling the air temperature of the air flowing from the central air conditioning unit 101 into the pipes and/or tubing 130 of the local climate control device 106. The local climate control device 106 further comprises absolute air humidity control unit 140 in fluid connection with pipe 130.

Figure 3B:
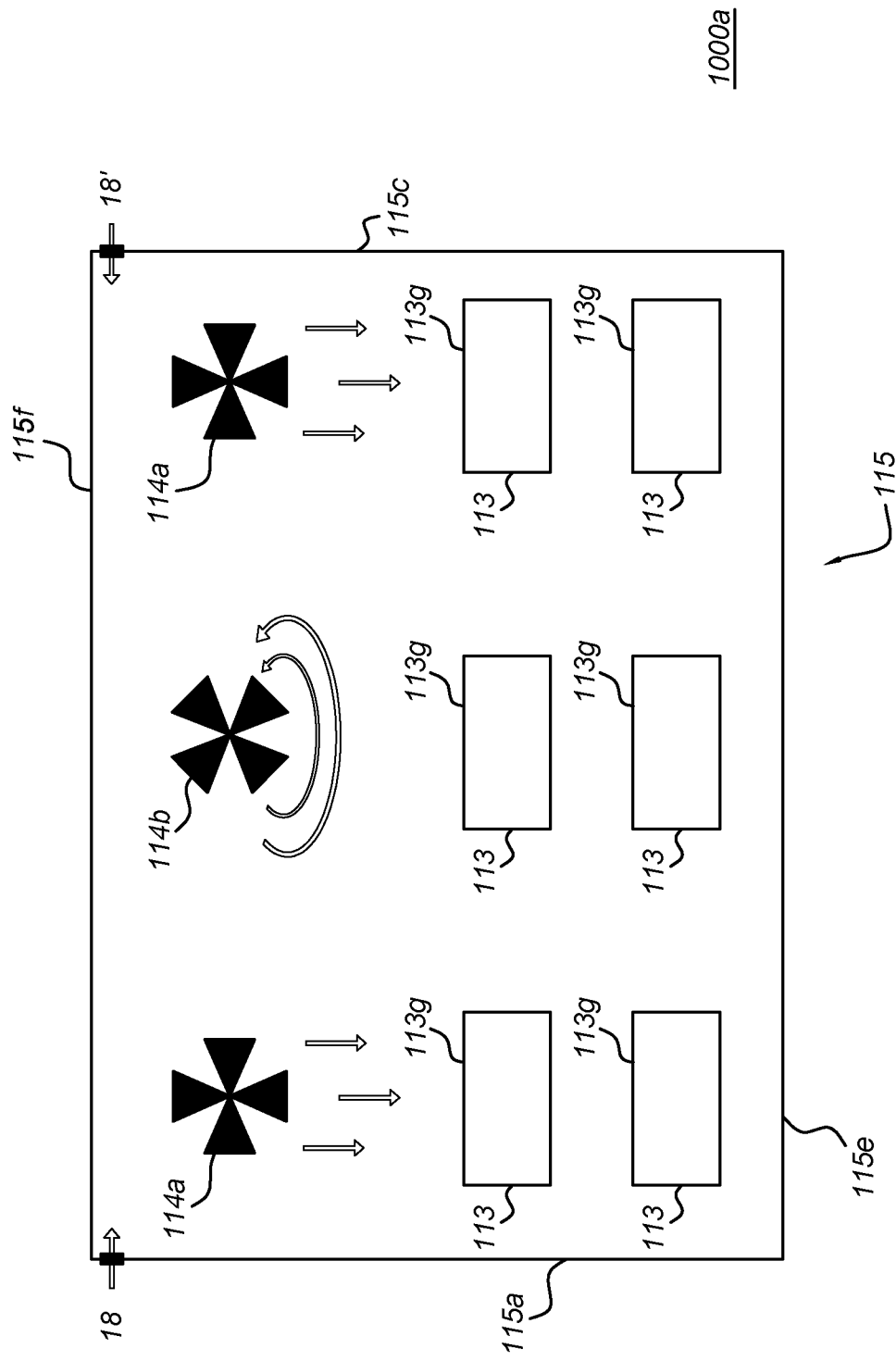

FIG. 3B displays insect farm climate control system 1000a, containing at least one cluster of insect cages, comprising at least two insect cages 113. The cages 113 have a top side 113g. The insect cages 113 are arranged vertically stacked and stacks of vertically stacked cages are arranged horizontally, side by side, preferentially evenly filling the floor space 115e and evenly filling the volume of farming room 115. The farming room 115 is heat insulated and/or the insect cages 113 are heat insulated. For example, at least the farming room 115 is heat insulated. Ambient air or temperature controlled air, or temperature controlled and/or absolute air humidity controlled air is driven into the insulated farming room 115 through an inlet 18, 18', 118 (See also FIG. 3A). Ambient air is for example entering the farming room 115 through inlets 18, 18', located near the ceiling 115f of the farming room 115, therewith providing an air stream towards fan 114b, located at or near the ceiling 115f, and homogenizing the air inside the farming room 115 horizontally, i.e. in horizontal direction. Further one or more fans 114a are also located at or near ceiling 115f, and are configured to homogenize the air inside farming room 115 vertically, i.e. in vertical direction. As a result, farming room 115 is homogenously filled with ambient air, or temperature controlled air, or temperature controlled and absolute air humidity controlled air. Typically, farming room 115 is heat insulated, whereas the insect cages 113 may or may not be heat insulated. For example, the air entering farming room 115 through inlets 18, 18', 118 is temperature controlled air. The insect cages 113 are connected to the local climate control device 106 for the provision of temperature controlled and absolute air humidity controlled air inside the insect cages 113. The temperature of the homogenized air in farming room 115, homogenized by fans 114a, 114b, is substantially the same as the temperature of the conditioned air provided by the local climate control device 106. The homogenized air inside the farming room 115 is for example provided by the farming room climate control device 128. The inventors established that the air temperature inside insect cages 113 is determined to a major extent by the air temperature of the air in the farming room 115 surrounding the insect cages 113, and to a lesser extent by the air temperature driven through the insect cages 113 by drivers 120b, 122. An efficient approach for controlling and maintaining air temperature inside the insect cages 113 within a relatively small temperature range was established by the provision of an insulated farming room 115, wherein the insect cages 113 are not significantly insulated, and wherein temperature controlled air or ambient air is provided to the interior of the farming room 115 through inlet 18, 18' and/or by driver 120a through inlet 118, and temperature conditioned and humidity conditioned air is provided to the interior of the insect cages 113 by driver(s) 120b, 122. The controlled temperature inside the insect cages 113 is thus controllable and can be maintained within a range as small as less than 1° C., such as less than 0.5° C. or less than 0.25° C. The temperature is typically between 25° C. and 33° C. For example, the absolute temperature of the homogenized air in the farming room 115 and the absolute temperature of the air driven through the insect cages 113 is between 31° C. and 33° C. Typically, the temperature difference between the air surrounding the insect cages 113 in the farming room 115 and the air driven through the insect cages 113, when inside the insect cages 113, is about 0.2° C. or less. For example, the temperature in the farming room 115 and the temperature inside the insect cages 113 is about 31.8° C.±0.22° C. A similar tight temperature control when the air temperature inside the insect cages 113 is considered, is established when pipes transporting air towards the insect cages 113 are heat insulated, optionally combined with the insect cages 113 being heat-insulated cages 113, wherein the air surrounding the insect cages 113 is for example ambient air at ambient temperature.

Figure 4:
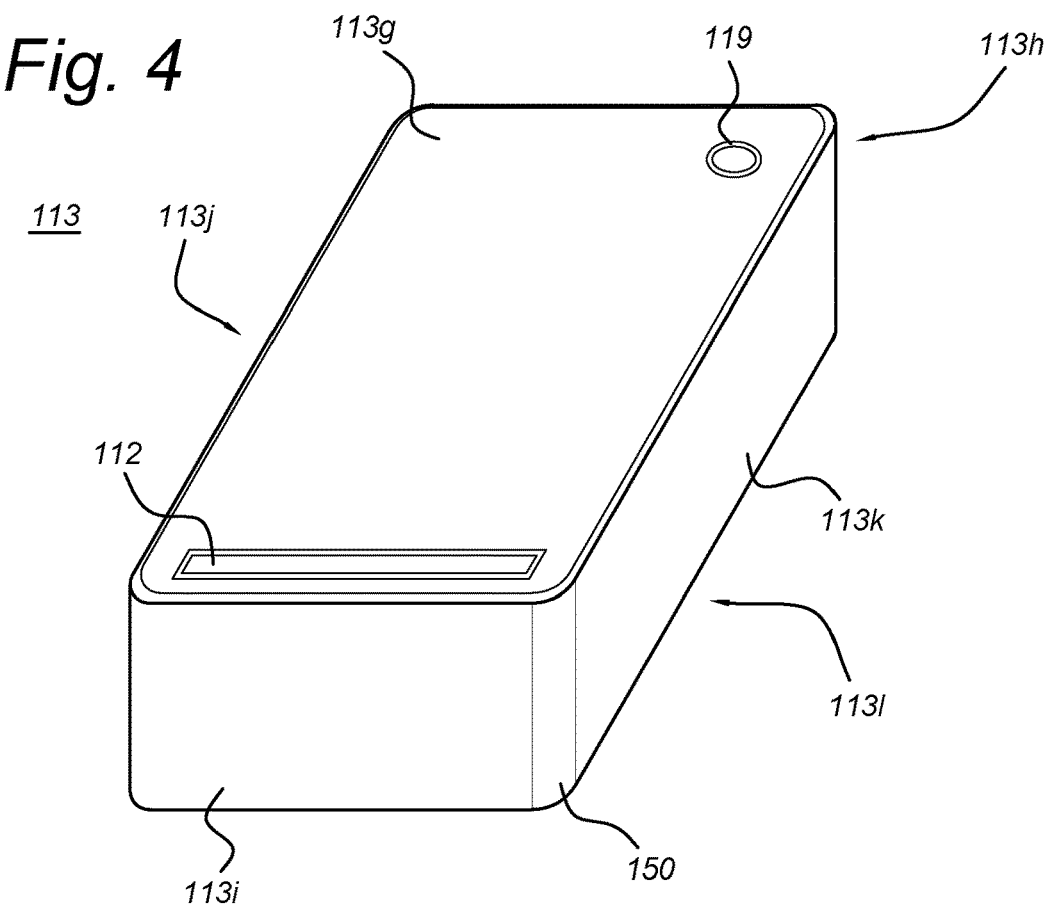
In FIG. 4 and FIG. 5, preferred embodiments are shown of the at least one insect cage comprised by the at least one cluster of cages in the adult insect cage climate control system of the invention.

Turning to FIG. 4, shown is an embodiment of one insect cage 113 comprised by a cluster of insect cages as part of the adult insect cage climate control system of the invention. The cage 113 has a top side 113g, a back side 113h, side walls 113j and 113k, bottom side 113l and front wall 113i. The insect cage 113 has rounded corners 150 at the exterior and interior of the cage. In top side 113g of the insect cage an air inlet opening 112 is provided configured to receive a pipe 131 for providing flow 127 of temperature conditioned and relative air humidity conditioned air into the cage 113. Air inlet opening 112 is located in the proximity of the front wall 113i of insect cage 113, wherein the air inlet opening 112 spans between about 40% and 100% of the width of the top side 113g measured from side wall 113j to 113k, the location and size of said air inlet opening 112 allowing for a flow of conditioned air in the direction from the front wall 113i towards the back side 113h, to an air outlet opening 119, located in the top side 113g of insect cage 113, near the back side 113h. For example opening 112 is located in top side 113g at a distance of between 0% and 15% from the front wall 113i measured from the top side of the front wall 113i. For example opening 119 is located in the top side 113g at a distance of between 0% and 15% from the back side 113h measured from the top side of the back side 113h, and at a distance of between 0% and 15% from either the side wall 113j, or the side wall 113k, measured from the top side of the side wall.

Figure 5:
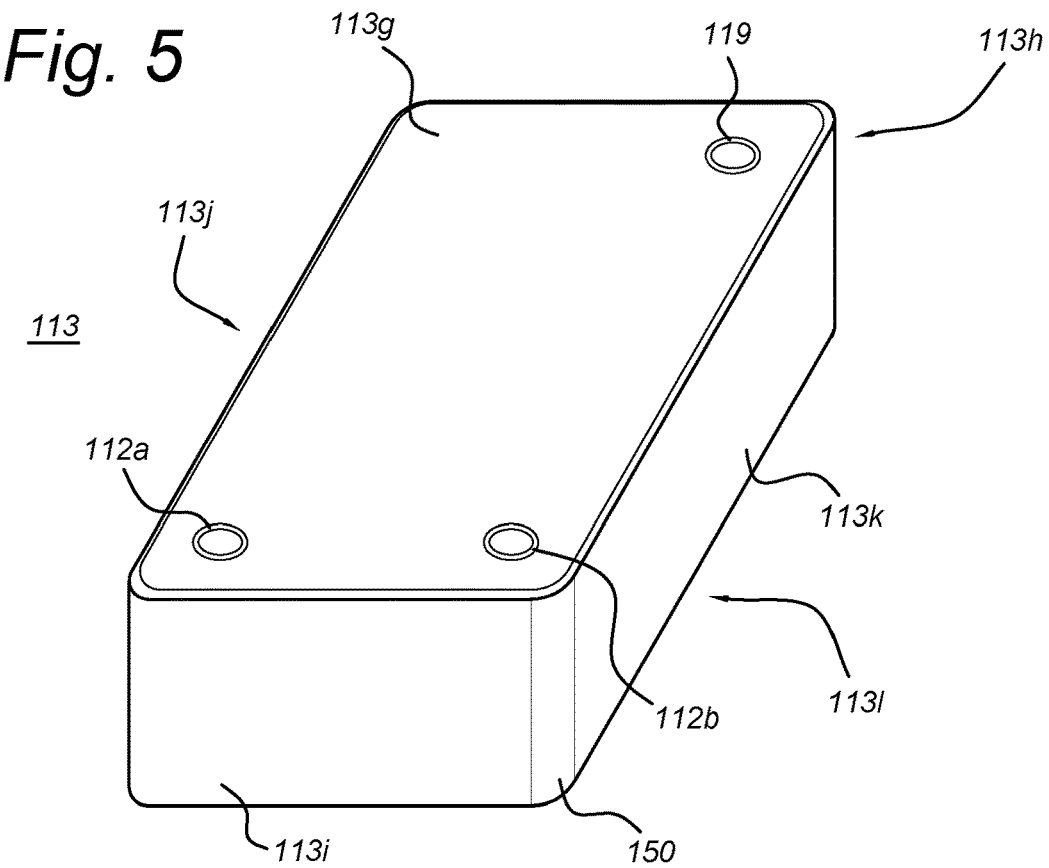

Turning to FIG. 5, shown is an embodiment of one insect cage 113 comprised by a cluster of insect cages as part of the adult insect cage climate control system of the invention. The cage 113 has a top side 113g, a back side 113h, side walls 113j and 113k, bottom side 113l and front wall 113i. The insect cage 113 has rounded corners 150 at the exterior and interior of the cage. In top side 113g of the insect cage at least one air inlet opening 112a, 112b is provided configured to receive a pipe 131 for providing flow 127 of temperature conditioned and relative air humidity conditioned air into the cage 113. The at least one air inlet opening 112a, 112b is/are located in the proximity of the front wall 113i of insect cage 113, wherein the air inlet openings 112a, 112b are evenly distributed over the width of the top side 113g measured from side wall 113j to 113k, the location and size of said at least one air inlet opening 112a, 112b allowing for a flow of conditioned air in the direction from the front wall 113i towards the back side 113h, to an air outlet opening 119, located in the top side 113g of insect cage 113, near the back side 113h. For example two air inlet openings 112a and 112b are located in top side 113g each at a distance of between 0% and 15% from the front wall 113i measured from the top side of the front wall 113i. For example opening 119 is located in the top side 113g at a distance of between 0% and 15% from the back side 113h measured from the top side of the back side 113h, and at a distance of between 0% and 15% from either the side wall 113j, or the side wall 113k, measured from the top side of the side wall. Air outlet opening 119 is configured to connect to pipe 167.

While the invention has been described in terms of several embodiments, it is contemplated that alternatives, modifications, permutations and equivalents thereof will become apparent to one having ordinary skill in the art upon reading the specification and upon study of the drawings. The invention is not limited in any way to the illustrated embodiments. Changes can be made without departing from the scope which is defined by the appended claims.

The invention claimed is:

1. An adult insect cage climate control system comprising:
    a local climate control device;
    at least one cluster of cages, said at least one cluster of cages comprising at least two insect cages, each insect cage comprising at least one air inlet opening and at least one air outlet opening;
    a first pipe connected to a first air temperature control unit and connected to the local climate control device for providing the local climate control device with temperature controlled air;
    a second pipe connected to the first air temperature control unit;
    an absolute air humidity control unit in fluid connection with second pipe;
    a first driver for driving conditioned air in fluid connection with the second pipe and in fluid connection with a fourth pipe, for pushing conditioned air through the insect cage(s), and/or a second driver in fluid connection with the at least one air outlet opening, for drawing conditioned air through the insect cage(s),
    wherein the fourth pipe is in further fluid connection with a fifth pipe, the fifth pipe is in further fluid connection with a sixth pipe, and the sixth pipe is in further fluid connection with the at least one air inlet opening in each of the insect cages for providing a flow of conditioned air through the insect cages in a direction of the at least one air outlet opening in the cage surface opposite to the air inlet openings,
    wherein the adult insect cage climate control system is configured to controllably provide the at least two cages with an air flow through the cage(s) with an air temperature of between 25° C. and 38° C.

2. The adult insect cage climate control system according to claim 1, wherein an internal diameter of the fifth pipe is smaller than an internal diameter of the fourth pipe, and an internal diameter of the sixth pipe is smaller than the internal diameter of the fifth pipe.

3. The adult insect cage climate control system according to claim 1, wherein the pipe or pipes connecting the second pipe with the at least one air inlet opening of each insect cage comprise tapered internal diameter(s) with decreasing internal diameter in a direction from the second pipe towards the at least one air inlet opening.

4. The adult insect cage climate control system according to claim 1, wherein the at least one air outlet opening is in fluid connection with a fifteenth pipe connected to a seventh pipe, for transporting conditioned air exiting the insect cages, the seventh pipe is in further fluid connection with an eighth pipe, wherein an internal diameter of the eighth pipe is larger than an internal diameter of the seventh pipe and the internal diameter of the seventh pipe is larger than an internal diameter of the fifteenth pipe.

5. The adult insect cage climate control system according to claim 1, wherein the pipe or pipes connected to the at least one air outlet opening of each insect cage comprise tapered internal diameter(s) with increasing internal diameter in a direction from the at least one air outlet opening towards a proximal end of said connected pipe or pipes.

6. The adult insect cage climate control system according to claim 1, wherein each insect cage comprises a top side, a back side, side walls, bottom side and front wall, wherein preferably the sides and/or walls are impermeable for air and/or for moisture, more preferably the sides and the walls are impermeable for air and for moisture.

7. The adult insect cage climate control system according to claim 1, wherein valves are provided in any of the fourth pipe, the fifth pipe or the sixth pipe for controlling transport of conditioned air from the first driver to each of the at least two insect cages comprised by a cluster of cages.

8. The adult insect cage climate control system according to claim 1, further comprising an insect farming room climate control device and an insect farming room with side walls, floor and ceiling, said insect farming room containing the at least two insect cages comprised by at least one cluster of cages,
    the insect farming room climate control device comprising a ninth pipe in fluid connection with a second air temperature control unit and a third driver and the ninth pipe in further fluid connection with air inlet opening of farming room to allow a flow of temperature controlled air into the farming room,
    the farming room further comprising an air outlet opening for connecting an eighth pipe with a tenth pipe, for transportation of conditioned air from the farming room outwardly,
    and said farming room further comprising an air inlet opening for connecting the second pipe of the local climate control device with the fourth pipe.

9. The adult insect cage climate control system according to claim 8, wherein the insect farming room further comprises at least one fan for homogenizing the air inside the insect farming room, and/or one first fan configured to horizontally homogenize the air and/or at least one second fan configured to vertically homogenize the air.

10. The adult insect cage climate control system according to claim 8, wherein the adult insect cage climate control system is configured to maintain the air temperature inside the insect farming room within a temperature range of 2° C. or less, preferably within a temperature range of 1° C. or less, and/or to provide the insect farming room with an air flow through the insect farming room with a temperature of between 25° C. and 38° C.

11. The adult insect cage climate control system according to claim 1, wherein the local climate control device further comprises an air filtering device in fluid connection with a tenth pipe and in fluid connection with an eleventh pipe, said eleventh pipe connected to a third air temperature control unit, for recirculation of at least part of the conditioned air driven through the at least one cluster of insect cages.

12. The adult insect cage climate control system according to claim 1, further comprising a central air conditioning unit provided with a twelfth pipe in fluid connection with an air driver device, and in fluid connection with an absolute air humidity control unit and a thirteenth pipe, said thirteenth pipe in fluid connection with least one air temperature control unit in fluid connection with the first pipe, for driving temperature controlled and absolute air humidity controlled air to at least one local climate control system.

13. The adult insect cage climate control system according to claim 12, wherein the first pipe comprises a valve for controlling the flow of temperature controlled and absolute air humidity controlled air from the central air conditioning unit to the at least one local climate control system.

14. The adult insect cage climate control system according to claim 12, wherein the central air conditioning unit further comprises an air heat exchange device coupled to a fourteenth pipe in fluid connection with an eighth pipe, said air heat exchange device configured to allow heat exchange from air driven through the eighth pipe to air drawn into the driver device of the central air conditioning unit through the twelfth pipe.

15. The adult insect cage climate control system according to claim 12, wherein the absolute air humidity control unit is configured to controllably provide the at least two cages with an air flow through the cages with an absolute air humidity of between 5 gram $H_2O$/kg air and 46 gram $H_2O$/kg air at an air temperature of between 25° C. and 38° C. at atmospheric pressure of 1.0 bar, preferably an absolute air humidity of between 10 gram $H_2O$/kg air and 30 gram $H_2O$/kg air at an air temperature of between 28° C. and 35° C., preferably between 29° C. and 34° C., more preferably between 31° C. and 33° C., at atmospheric pressure of 1.0 bar.

16. The adult insect cage climate control system according to claim 1, wherein the adult insect cage climate control system is configured to maintain the air temperature inside the at least two cages within a temperature range of 2° C. or less, preferably within a temperature range of 1° C. or less.

17. The adult insect cage climate control system according to claim 1, wherein the adult insect cage climate control system is configured to controllably provide the at least two cages with an air flow through the cages of between 10 $m^3$/hour and 200 $m^3$/hour, preferably about 100 $m^3$/hour, more preferably about 45 $m^3$/hour, and/or at an air temperature of between 28° C. and 35° C.

18. The adult insect cage climate control system according to claim 1, wherein the cages are heat insulated cages, and/or wherein one or more of the pipes are heat insulated.

19. The adult insect cage climate control system according to claim 1, wherein the at least two cages are cages comprising rounded corners at least at an interior side, and/or are blow molded cages or rotation molded cages made of a polymer or polymer blend.

20. The adult insect cage climate control system according to claim 1, wherein the second pipe has an internal diameter of between 100 mm and 400 mm, and/or the fourth pipe has an internal diameter of between 125 mm and 500 mm, and/or the fifth pipe has an internal diameter of between 80 mm and 320 mm, and/or the sixth pipe has an internal diameter of between 40 mm and 160 mm, and/or a fifteenth pipe has an internal diameter of between 45 mm and 180 mm, and/or a seventh pipe has an internal diameter of between 80 mm and 320 mm, and/or an eighth pipe has an internal diameter of between 100 mm and 400 mm.

\* \* \* \* \*